US00PP28616P3

(12) United States Plant Patent
de Bont

(10) Patent No.: US PP28,616 P3
(45) Date of Patent: Nov. 7, 2017

(54) ***ECHINACEA* PLANT NAMED 'HILMOOOCOSY'**

(50) Latin Name: *Echinacea purpurea*
Varietal Denomination: Hilmooocosy

(71) Applicant: Diony de Bont, De Kwakel (NL)

(72) Inventor: Diony de Bont, De Kwakel (NL)

(73) Assignee: Takii Europe B.V., De Kwakel (NL)

( * ) Notice: Subject to any disclaimer, the term of this patent is extended or adjusted under 35 U.S.C. 154(b) by 61 days.

(21) Appl. No.: 14/756,667

(22) Filed: Sep. 29, 2015

(65) Prior Publication Data

US 2017/0094885 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

De Boomkwekerij 2014 Plantarium shows more that 110 new varieties, retrieved on Jan. 23, 2017, retrieved from the Internet at <https://issuu.com/hortipoint/docs/bkw_17a-2014vv> pp. 11 and 19.*

* cited by examiner

*Primary Examiner* — June Hwu
(74) *Attorney, Agent, or Firm* — C. A. Whealy

(57) ABSTRACT

A new and distinct cultivar of *Echinacea* plant named 'Hilmooocosy', characterized by its upright and relatively compact plant habit; moderately vigorous growth habit; strong and healthy roots; dark green-colored leaves; strong flowering stems; numerous large inflorescences with dark pink-colored ray florets; and good garden performance.

1 Drawing Sheet

Botanical designation: *Echinacea purpurea.*
Cultivar denomination: 'HILMOOOCOSY'.

BACKGROUND OF THE INVENTION

The present invention relates to a new and distinct cultivar of *Echinacea* plant, botanically known as *Echinacea purpurea*, and hereinafter referred to by the name 'Hilmooocosy'.

The new *Echinacea* plant is a product of a planned breeding program conducted by the Inventor in De Kwakel, The Netherlands. The objective of the breeding program is to develop new strong and freely flowering *Echinacea* plants with attractive ray and disc floret coloration.

The new *Echinacea* plant originated from an open-pollination in June, 2009 in De Kwakel, The Netherlands of a proprietary selection of *Echinacea purpurea* identified as code designation T 14061 A, not patented, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in De Kwakel, The Netherlands in July, 2010.

Asexual reproduction of the new *Echinacea* plant by in vitro meristem culture in a controlled environment in De Kwakel, The Netherlands since September, 2010 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilmooocosy'. These characteristics in combination distinguish 'Hilmooocosy' as a new and distinct *Echinacea* plant:

1. Upright and relatively compact plant habit.
2. Moderately vigorous growth habit.
3. Strong and healthy roots.
4. Dark green-colored leaves.
5. Strong flowering stems.
6. Numerous large inflorescences with dark pink-colored ray florets.
7. Good garden performance.

Plants of the new *Echinacea* can be compared to plants of the female parent selection. Plants of the new *Echinacea* differ from plants of the female parent selection in the following characteristics:

1. Plants of the new *Echinacea* are more compact than plants of the female parent selection.
2. Plants of the new *Echinacea* have smaller leaves than plants of the female parent selection.
3. Plants of the new *Echinacea* have smaller inflorescences than plants of the female parent selection.
4. Ray florets of plants of the new *Echinacea* are lighter pink in color than ray florets of plants of the female parent selection.

Plants of the new *Echinacea* can be compared to plants of *Echinacea purpurea* 'Kim's Knee High', disclosed in U.S. Plant Pat. No. 12,242. In side-by-side comparisons conducted in De Kwakel, The Netherlands, plants of the new *Echinacea* differed primarily from plants of 'Kim's Knee High' in the following characteristics:

1. Plants of the new *Echinacea* were more compact than plants of 'Kim's Knee High'.
2. Plants of the new *Echinacea* had stronger and healthier roots and leaves than plants of 'Kim's Knee High'.
3. Plants of the new *Echinacea* were more freely branching than plants of 'Kim's Knee High'.
4. Plants of the new *Echinacea* had smaller inflorescences than plants of 'Kim's Knee High'.

BRIEF DESCRIPTION OF THE PHOTOGRAPH

The accompanying photograph illustrates the overall appearance of the new *Echinacea* plant showing the colors as true as it is reasonably possible to obtain in colored reproductions of this type. Colors in the photograph may differ slightly from the color values cited in the detailed botanical description which accurately describe the colors of the new *Echinacea* plant.

The photograph is a side perspective view of a typical flowering plant of 'Hilmooocosy' grown in a container.

DETAILED BOTANICAL DESCRIPTION

The aforementioned photograph and following observations and measurements describe plants grown during the spring and early summer in 17-cm containers in a glass-covered greenhouse and "finished" in an outdoor nursery in De Kwakel, The Netherlands under cultural practices typically used in commercial *Echinacea* production. During the production of the plants, day temperatures ranged from 12° C. to 20° C. and night temperatures ranged from 7° C. to 15° C. Plants used for the photograph and description were 20 weeks old. In the following description, color references are made to The Royal Horticultural Society Colour Chart, 2007 Edition, except where general terms of ordinary dictionary significance are used.

Botanical classification: *Echinacea purpurea* 'Hilmooocosy'.

Parentage:

*Female parent*.—Proprietary selection of *Echinacea purpurea* identified as code designation T 14061 A, not patented.

*Male parent*.—Unknown selection of *Echinacea purpurea*, not patented.

Propagation:

*Type*.—By in vitro meristem culture.

*Time to initiate roots, summer*.—About five weeks at temperatures about 20° C. for the first two weeks, then at temperatures about 12° C. to 14° C.

*Time to initiate roots, winter*.—About six weeks at temperatures about 20° C. for the first two weeks, then at temperatures about 14° C. to 20° C.

*Time to produce a rooted young plant, summer*.—About five weeks at temperatures about 14° C. to 20° C.

*Time to produce a rooted young plant, winter*.—About six weeks at temperatures about 18° C.

*Root description*.—Medium in thickness, fibrous; strong and healthy; typically white to brown in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous perennial; upright and relatively compact plant habit, narrow inverted triangle; freely branching habit with about 17 branches developing per plant; moderately vigorous growth habit.

*Plant height*.—About 41 cm.

*Plant diameter or spread*.—About 33 cm.

*Lateral branches*.—Length: About 21.5 cm. Diameter: About 8 mm. Internode length: About 2.2 cm. Aspect: Erect to about 10° from vertical. Strength: Strong. Texture: Sparsely pubescent, strigose; rough. Color: Close to 200A to 200B.

Leaf description:

*Basal leaves*.—Arrangement: Alternate, simple. Length: About 11 cm. Width: About 3.9 cm. Shape: Narrowly ovate. Apex: Acute. Base: Long attenuate. Margin: Entire; moderately undulate. Texture, upper and lower surfaces: Moderately to densely pubescent, strigose; rough. Luster, upper surface: Slightly glossy. Luster, lower surface: Moderately glossy. Venation pattern: Pinnate. Color: Developing leaves, upper surface: Close to between N137B and 143A. Developing leaves, lower surface: Close to between 146A to 147B. Fully expanded leaves, upper surface: Close to between N137A to 147A; venation, close to 177A slightly tinged with close to 152C. Fully expanded leaves, lower surface: Close to between 146A and 147B; venation, close to 145B.

*Petioles, basal leaves*.—Length: About 3.7 cm. Diameter: About 4 mm. Strength: Strong, flexible. Texture, upper and lower surfaces: Smooth, glabrous. Color, upper surface: Close to 177A; margins, close to N137B. Color, lower surface: Close to 144B; margins, close to N137A.

*Cauline leaves*.—Arrangement: Alternate, simple. Length: About 5.5 cm. Width: About 2.2 cm. Shape: Narrowly ovate. Apex: Narrowly acute. Base: Attenuate. Margin: Entire. Texture, upper and lower surfaces: Moderately to densely pubescent, strigose; rough. Luster, upper surface: Slightly glossy. Luster, lower surface: Moderately glossy. Venation pattern: Pinnate. Color: Developing leaves, upper surface: Close to between N137B and 143A. Developing leaves, lower surface: Close to between 146A and 147B. Fully expanded leaves, upper surface: Close to between N137A and 147A; venation, close to 177A slightly tinged with close to 152C. Fully expanded leaves, lower surface: Close to between 146A and 147B; venation, close to 145B.

*Petioles, cauline leaves*.—Length: About 8 mm. Diameter: About 2 mm. Strength: Strong, flexible. Texture, upper and lower surfaces: Moderately to densely pubescent; rough. Color, upper surface: Close to between N137A and 147A. Color, lower surface: Close to between 146A and 147B.

Inflorescence description:

*Appearance*.—Terminal rotate single-type inflorescences with ray and disc florets arranged on a capitulum; inflorescences positioned upright above the foliar plane on mostly upright and strong peduncles.

*Flowering habit*.—Freely flowering habit with about 17 inflorescences per plant at one time.

*Fragrance*.—Faint; sweet, pleasant.

*Time to flower*.—Plants begin flowering about 13 to 18 weeks after planting; in the garden, plants flower continuously from mid-June to late September in The Netherlands.

*Inflorescence longevity*.—Inflorescences maintain good substance for about three weeks on the plant; inflorescences persistent.

*Inflorescence buds*.—Height: About 1.9 cm. Diameter: About 3 cm. Shape: Flattened globular. Color: Involucral bracts, close to 143A and 137B; ray florets, close to 52B, towards the base, close to 150C.

*Inflorescence size*.—Diameter: About 8.5 cm. Depth (height): About 3.2 cm. Disc diameter: About 3.4 cm. Receptacle height: About 1.5 cm. Receptacle diameter: About 1.1 cm. Receptacle color: Close to 155C slightly tinged with close to 64A to 64B.

*Ray florets*.—Quantity and arrangement: About 18 arranged in a single whorl at the base of the receptacle. Length: About 3.8 cm. Width: About 1.2 cm. Shape: Oblanceolate to narrowly ovate. Apex: Praemorse. Base: Cuneate. Margin: Entire. Texture, upper surface: Smooth, glabrous; moderately velvety. Texture, lower surface: Smooth, glabrous. Luster, upper surface: Matte. Luster, lower surface: Slightly glossy. Aspect: Horizontal to drooping, about 10° from horizontal. Color: When opening, upper surface: Close to 67A; towards the apex, close to 67B; towards the base, close to 61B. When opening, lower surface: Close to 59D. Fully opened, upper surface: Close to 64B; towards the base, close to 61B; color becoming closer to 64C to 64D with development. Fully opened, lower surface: Close to 60C to 60D; color becoming closer to 60D with development.

*Disc florets*.—Length: About 6 mm. Diameter: About 3.5 mm. Shape: Tubular, apices acute. Number of disc florets per inflorescence: About 400. Texture, inner and outer surfaces: Smooth, glabrous. Luster, inner and outer surfaces: Glossy. Color, immature, inner and outer surfaces: Apex: Close to 144B tinged with close to 180B. Mid-section: Close to 152C. Base: Close to 144B. Color, mature, inner and outer surfaces: Apex and mid-section: Close to 182B tinged with close to 181A. Base: Close to 146D.

*Receptacle spines*.—Quantity: One per disc floret. Shape: Acicular. Apex: Narrowly acute. Base: Attenuate. Texture: Smooth, glabrous. Luster: Glossy. Color: Apex: Close to N30B to N30C; at the apex, close to 46A. Mid-section: Close to 143B. Base: Close to 145B.

*Involucral bracts*.—Quantity per inflorescence: About 64 arranged in about four whorls. Length: About 9 mm. Width: About 3 mm. Shape: Ovate to narrowly ovate. Apex: Acute. Base: Cuneate. Margin: Entire. Texture, upper surface: Smooth, glabrous. Texture, lower surface: Moderately to densely pubescent. Color, upper surface: Close to 146A. Color, lower surface: Close to 138A.

*Peduncles*.—Length: About 12.2 cm. Diameter: About 6 mm. Strength: Strong. Aspect: Upright. Texture: Moderately pubescent, strigose. Color: Close to 200C tinged with close to 146A.

*Reproductive organs*.—Androecium (present on ray and disc florets): Quantity per floret: About five. Filament length: About 6 mm. Filament color: Close to 150D. Anther shape: Narrowly oblong. Anther length: About 3 mm. Anther color: Close to N200A to N200B. Pollen amount: Scarce. Pollen color: Close to 17B. Gynoecium (present only on disc florets): Quantity per floret: One. Pistil length: About 7 mm. Stigma shape: Decurrent, unequal. Stigma color: Close to 187A. Style length: About 5.5 mm. Style color: Close to 185A. Ovary color: Close to 145D. Seeds and fruits: Seed and fruit development have not been observed on plants of the new *Echinacea*.

Disease & pest resistance: Plants of the new *Echinacea* have not been shown to be resistant to pathogens and pests common to *Echinacea*.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Hilmoooocosy' as illustrated and described.

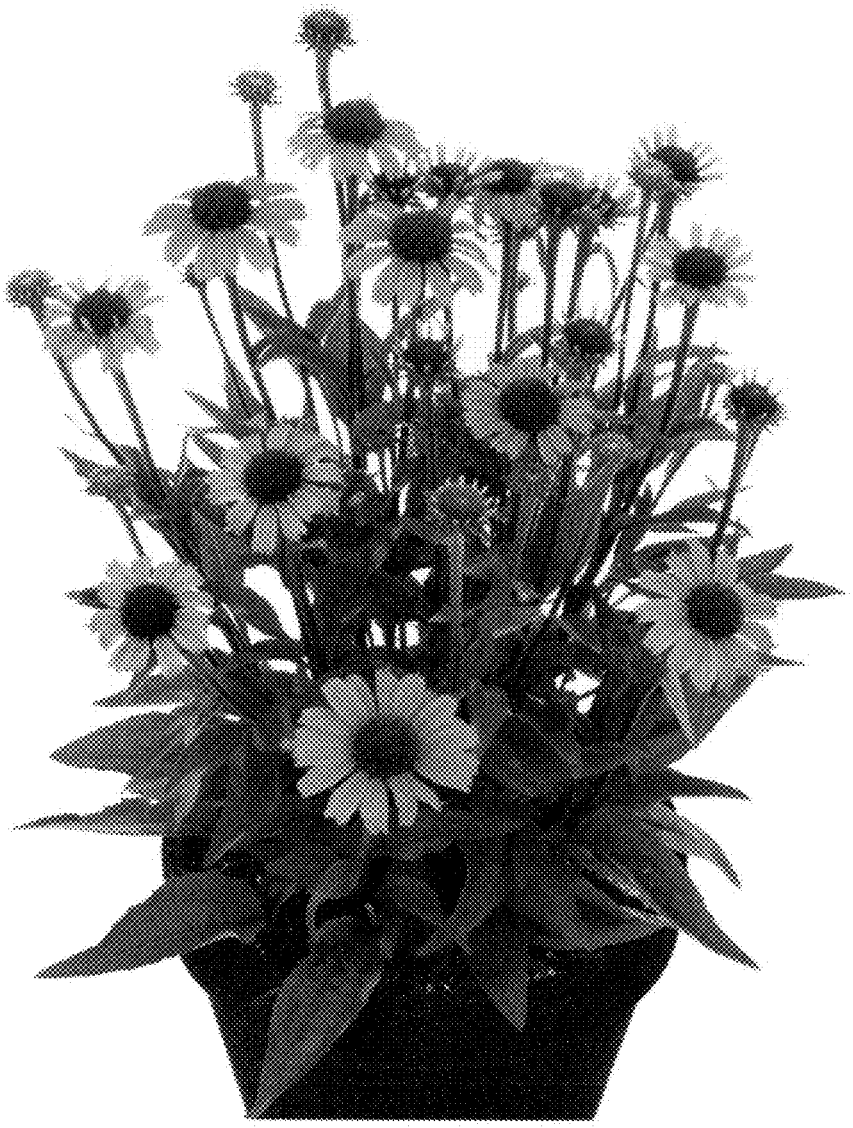

* * * * *